US007291253B2

(12) United States Patent
Pavlov et al.

(10) Patent No.: US 7,291,253 B2
(45) Date of Patent: Nov. 6, 2007

(54) DETECTION OF AN UNSTABLE ADDITIVE BREAKDOWN PRODUCT IN A PLATING BATH

(75) Inventors: Michael Pavlov, Fairlawn, NJ (US); Eugene Shalyt, Washington Township, NJ (US); Peter Bratin, Flushing, NY (US)

(73) Assignee: ECI Technology, Inc., Totowa, NJ (US)

( * ) Notice: Subject to any disclaimer, the term of this patent is extended or adjusted under 35 U.S.C. 154(b) by 466 days.

(21) Appl. No.: 10/838,803

(22) Filed: May 4, 2004

(65) Prior Publication Data
US 2005/0247577 A1    Nov. 10, 2005

(51) Int. Cl.
    C25D 21/00    (2006.01)
(52) U.S. Cl. ............ 205/81; 205/793.5; 205/794; 205/786.5; 205/787
(58) Field of Classification Search ........... 205/81–82, 205/99, 123, 786.5, 787, 793.5, 794; 204/434
See application file for complete search history.

(56) References Cited

U.S. PATENT DOCUMENTS

| 3,985,784 | A | * | 10/1976 | Clauss et al. .......... 558/437 |
| 4,132,605 | A |   | 1/1979  | Tench et al. |
| 6,491,806 | B1 | * | 12/2002 | Dubin et al. .......... 205/296 |
| 6,508,924 | B1 | * | 1/2003  | Gomez et al. .......... 205/81 |
| 6,527,920 | B1 | * | 3/2003  | Mayer et al. .......... 204/237 |
| 6,572,753 | B2 | * | 6/2003  | Chalyt et al. .......... 205/81 |
| 2003/0062266 | A1 | * | 4/2003 | Chalyt et al. .......... 205/81 |
| 2004/0000484 | A1 | * | 1/2004 | Sun et al. .......... 205/81 |
| 2004/0065561 | A1 | * | 4/2004 | Chalyt et al. .......... 205/775 |
| 2004/0108213 | A1 | * | 6/2004 | Talasek et al. .......... 205/81 |

OTHER PUBLICATIONS

Tench, D. et al. "A New Voltammetric Stripping Method Applied to the Determination of the Brightener Concentration in Copper Pyrophosphate Plating Baths", J. Electrochem. Soc. 125, 194 (1978).
Haak, R. et al. "Cyclic Voltammetric Stripping Analysis of Acid Copper Sulfate Plating Baths, Part I: Polyether-Sulfide-Based Additives", Plating Surf Fin 68(4) 52 (1981).
Haak, R. et al. "Cyclic Voltammetric Stripping Analysis of Acid Copper Sulfate Plating Baths, Part II: Sulfoniumalkanesulfonate-Based Additives", Plating Surf. Fin. 69(3), 62 (1982).
Freitag, W. O. et al. "Determination of the Individual Additive Components in Acid Copper Plating Baths", Plating Surf. Fin. 70(10), 55 (1983).

(Continued)

*Primary Examiner*—Nam Nguyen
*Assistant Examiner*—Surekha Vathyam
(74) *Attorney, Agent, or Firm*—D. Morgan Tench

(57) ABSTRACT

The 3-mercaptopropylsulfonic acid (MPSA) breakdown product of the bis(sodiumsulfopropyl)disulfide (SPS) additive used in acid copper plating baths accelerates copper electrodeposition and can be detected by cyclic voltammetric stripping (CVS) analysis. In the presence of oxygen, MPSA decomposes rapidly in acid copper sulfate baths so that the CVS stripping peak area ($A_r$) decreases on successive cycles. The slope of a plot of $A_r$ vs. CVS cycle number (or time) or logarithm of the CVS cycle number (or time) provides a measure of the initial MPSA concentration.

26 Claims, 5 Drawing Sheets

OTHER PUBLICATIONS

Ogden, C. et al. "Cyclic Voltammetric Stripping Analysis of Copper Plating Baths", Application of Polarization Measurements in the Control of Metal Deposition. I. H. Warren, ed., Elsevier Science Publ. B. V., Amsterdam, 229, (1984).

Tench, D. et al. "Cyclic Pulse Voltammetric Stripping Analysis of Acid Copper Plating Baths", J. Electrochem. Soc. 132, 831 (1985).

* cited by examiner

DETECTION OF AN UNSTABLE ADDITIVE BREAKDOWN PRODUCT IN A PLATING BATH

BACKGROUND OF THE INVENTION

1. Field of the Invention

This invention is concerned with analysis of organic additives and contaminants in plating baths as a means of providing control over the deposit properties.

2. Description of the Related Art

Electroplating baths typically contain organic additives whose concentrations must be closely controlled in the low parts per million range in order to attain the desired deposit properties and morphology. One of the key functions of such additives is to level the deposit by suppressing the electrodeposition rate at protruding areas in the substrate surface and/or by accelerating the electrodeposition rate in recessed areas. Accelerated deposition may result from mass-transport-limited depletion of a suppressor additive species that is rapidly consumed in the electrodeposition process, or from accumulation of an accelerating species that is consumed with low efficiency. The most sensitive methods available for detecting leveling additives in plating baths involve electrochemical measurement of the metal electrodeposition rate under controlled hydrodynamic conditions for which the additive concentration in the vicinity of the electrode surface is well-defined.

Cyclic voltammetric stripping (CVS) analysis [D. Tench and C. Ogden, J. Electrochem. Soc. 125, 194 (1978)] is the most widely used bath additive control method and involves cycling the potential of an inert electrode (e.g., Pt) in the plating bath between fixed potential limits so that metal is alternately plated on and stripped from the electrode surface. Such potential cycling is designed to establish a steady state for the electrode surface so that reproducible results are obtained. Accumulation of organic films or other contaminants on the electrode surface can be avoided by periodically cycling the potential of the electrode in the plating solution without organic additives and, if necessary, polishing the electrode using a fine abrasive. Cyclic pulse voltammetric stripping (CPVS), also called cyclic step voltammetric stripping (CSVS), is a variation of the CVS method that employs discrete changes in potential during the analysis to condition the electrode so as to improve the measurement precision [D. Tench and J. White, J. Electrochem. Soc. 132, 831 (1985)]. A rotating disk electrode configuration is typically employed for both CVS and CPVS analysis to provide controlled hydrodynamic conditions.

For CVS and CPVS analyses, the metal deposition rate may be determined from the current or charge passed during metal electrodeposition but it is usually advantageous to measure the charge associated with anodic stripping of the metal from the electrode. A typical CVS/CPVS rate parameter is the stripping peak area ($A_r$) for a predetermined electrode rotation rate. The CVS method was first applied to control copper pyrophosphate baths (U.S. Pat. No. 4,132,605 to Tench and Ogden) but has since been adapted for control of a variety of other plating systems, including the acid copper sulfate baths that are widely used by the electronics industry [e.g., R. Haak, C. Ogden and D. Tench, Plating Surf. Fin. 68(4), 52 (1981) and Plating Surf. Fin. 69(3), 62 (1982)].

Acid copper sulfate electroplating baths require a minimum of two types of organic additives to provide deposits with satisfactory properties and good leveling characteristics. The suppressor additive (also called the "polymer", "carrier", or "wetter", depending on the bath supplier) is typically a polymeric organic species, e.g., high molecular weight polyethylene or polypropylene glycol, which adsorbs strongly on the copper cathode surface to form a film that sharply increases the overpotential for copper deposition. This prevents uncontrolled copper plating that would result in powdery or nodular deposits. An anti-suppressor additive (also called the "brightener", "accelerator" or simply the "additive", depending on the bath supplier) is required to counter the suppressive effect of the suppressor and provide the accelerated deposition within substrate recesses needed for leveling. Plating bath vendors typically provide additive solutions that may contain additives of more than one type, as well as other organic and inorganic addition agents. The suppressor additive may be comprised of more than one chemical species and generally involves a range of molecular weights.

Acid copper sulfate baths have functioned well for plating the relatively large surface pads, through-holes and vias found on printed wiring boards (PWB's) and are currently being adapted for plating fine trenches and vias in dielectric material on semiconductor chips. The electronics industry is transitioning from aluminum to copper as the basic metallization for semiconductor integrated circuits (IC's) in order to increase device switching speed and enhance electromigration resistance. The leading technology for fabricating copper IC chips is the "Damascene" process (see, e.g., P. C. Andricacos, Electrochem. Soc. Interface, Spring 1999, p. 32; U.S. Pat. No. 4,789,648 to Chow et al.; U.S. Pat. No. 5,209,817 to Ahmad et al.), which depends on copper electroplating to provide complete filling of the fine features involved. The organic additives in the bath must be closely controlled since they provide the copper deposition rate differential required for bottom-up filling.

As the feature size for the Damascene process has shrunk below 0.2 µm, it has become necessary to utilize a third organic additive in the acid copper bath in order to avoid overplating the trenches and vias. Note that excess copper on Damascene plated wafers is typically removed by chemical mechanical polishing (CMP) but the copper layer must be uniform for the CMP process to be effective. The third additive is called the "leveler" (or "booster", depending on the bath supplier) and is typically an organic compound containing nitrogen or oxygen that also tends to decrease the copper plating rate. In order to attain good bottom-up filling and avoid overplating of ultra-fine chip features, the concentrations of all three additives must be accurately analyzed and controlled.

The suppressor, anti-suppressor and leveler concentrations in acid copper sulfate baths can all be determined by CVS analysis methods based on the effects that these additives exert on the copper electrodeposition rate. At the additive concentrations typically employed, the effect of the suppressor in reducing the copper deposition rate is usually much stronger than that of the leveler so that the concentration of the suppressor can be determined by the usual CVS response curve or dilution titration analysis [W. O. Freitag, C. Ogden, D. Tench and J. White, Plating Surf. Fin. 70(10), 55 (1983)]. Likewise, the anti-suppressor concentration can be determined by the linear approximation technique (LAT) or modified linear approximation technique (MLAT) described by R. Gluzman [Proc. $70^{th}$ Am. Electroplaters Soc. Tech. Conf., Sur/Fin, Indianapolis, Ind. (June 1983)]. A method for measuring the leveler concentration in the presence of interference from both the suppressor and anti-suppressor is described in U.S. Pat. No. 6,572,753 to Chalyt et al.

For proper functioning of acid copper plating baths, it is also necessary to control the concentrations of additive breakdown products generated by electrochemical and/or chemical reactions involving additive species. Such additive breakdown products may degrade the properties of the copper deposit by interfering with the functioning of the additive system and/or by inclusion in the deposit. Depending on whether or not they exhibit activity similar to that of the parent additive, breakdown products could be considered auxiliary additives, which complicate control of the additive system, or contaminants, which directly degrade the deposit properties. A CVS method for analysis of suppressor breakdown contaminants in acid copper baths is described in U.S. patent application Ser. No. 10/266,066 to Chalyt et al. (filed Oct. 7, 2002).

One widely used anti-suppressor additive is bis(sodiumsulfopropyl)disulfide (SPS), which is known to break down in acid copper plating baths to form the dimer 3-mercaptopropylsulfonic acid (MPSA) species [T. P. Moffat, B. Baker, D. Wheeler and D. Josell, Electrochem. Solid State Lett. 6(4), C59 (2003)]. The MPSA breakdown product is oxidized back to the SPS monomer in the presence of oxygen but detrimental concentrations of MPSA can accumulate in the bath under some conditions. A means of analyzing for MPSA is needed so that effective methods for avoiding excessive MPSA accumulation can be developed and implemented. For example, the bleed and feed rate could be optimized to avoid excessive MPSA accumulation while minimizing consumption of expensive plating solution and generation of environmentally objectionable waste. A method for detecting MPSA in copper electroplating baths might also be useful for measuring the concentrations of additive breakdown products exhibiting similar behavior in copper baths, or baths for electroplating other metals.

SUMMARY OF THE INVENTION

The present invention provides a method for measuring the concentration of an additive breakdown product in a plating bath for electrodepositing a metal. The method is useful for analysis of additive breakdown products that affect the metal electrodeposition rate and decompose as a function of time. In this method, a rate parameter for electrodeposition of the metal is measured at a plurality of times in the plating bath, or in a measurement solution comprising the plating bath. The concentration of the additive breakdown product in the plating bath, at a predetermined time, is determined from the slope of a plot of the metal electrodeposition rate parameter versus a time parameter. This slope may be used as a relative measure of the concentration of the additive breakdown product in the plating bath at the predetermined time. Alternatively, the absolute concentration of the additive breakdown product in the plating bath at the predetermined time may be determined by reference to a standard curve obtained by measuring the metal electrodeposition rate parameter for a supporting electrolyte of the plating bath at a plurality of times for a plurality of standard additions of the breakdown product to the supporting electrolyte. In a preferred embodiment, the metal electrodeposition rate parameter is measured by the CVS method and the time parameter is the CVS cycle number, or the logarithm of the CVS cycle number. The time parameter may also be time or the logarithm of time measured relative to a predetermined time, or may be another function of time, e.g., a quadratic function of time.

The method of the present invention may be used, for example, to measure the concentration of the 3-mercaptopropylsulfonic acid (MPSA) breakdown product of the bis(sodiumsulfopropyl)disulfide (SPS) anti-suppressor additive in an acid copper sulfate plating bath. In the presence of oxygen, MPSA decomposes rapidly in acid copper baths so that the CVS stripping peak area ($A_r$) decreases on successive CVS cycles. A plot of $A_r$ vs. CVS cycle number (or time) or logarithm of the CVS cycle number (or time) is typically linear and the slope of the plot may be, calibrated to provide a measure of the MPSA concentration at a specific CVS cycle number or time, at the beginning of the analysis, for example. The MPSA concentration at an earlier time, when the bath sample was withdrawn from the plating bath, for example, may be determined by extrapolation of the $A_r$ vs. time parameter plot.

The present invention enables anti-suppressor additive breakdown contaminants in acid copper baths to be analyzed and controlled so as to ensure acceptable copper electrodeposits while minimizing consumption of expensive plating solution and generation of environmentally objectionable waste. Such optimized plating bath performance may be attained via appropriate adjustments in the additive bleed and feed rates, and/or as-needed replacement of all or part of the plating bath. The present invention may also be used to optimize other plating parameters so as to avoid buildup of excessive concentrations of anti-suppressor breakdown contaminants. For example, aeration of the plating bath may be used to hasten decomposition of breakdown contaminants, or the duty cycle for the process may be modified to allow more time for decomposition of such contaminants.

Further features and advantages of the invention will be apparent to those skilled in the art from the following detailed description, taken together with the accompanying drawings.

DETAILED DESCRIPTION OF THE INVENTION

Figure 1:
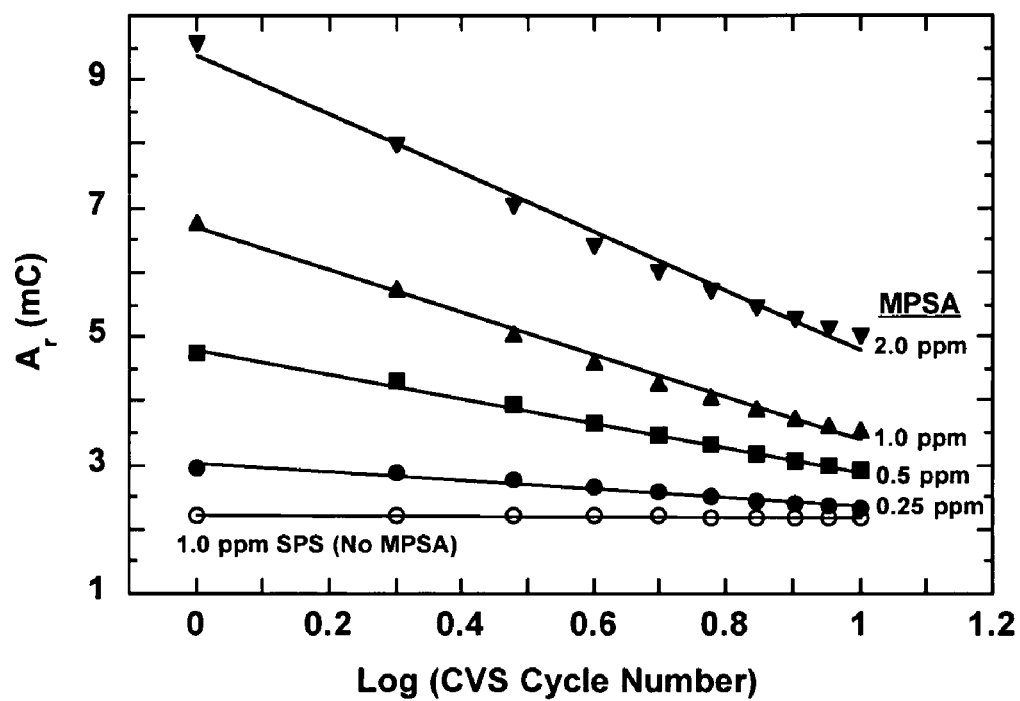
FIG. 1 shows plots of the CVS rate parameter $A_r$ vs. Log (CVS cycle number) as a function of initial MPSA concentration for acid copper supporting electrolyte containing 1.0 ppm of the SPS additive.

Technical terms used in this document are generally known to those skilled in the art. The term "electrode potential", or simply "potential", refers to the voltage occurring across a single electrode-electrolyte interface. In practice, the electrode potential often includes an appreciable resistive voltage drop in the electrolyte, which typically remains constant and does not affect voltammetric analysis results.

As used in this document, the terms "electroplating", "plating" and "electrodeposition" refer to metal electrodeposition and are equivalent. A "plating bath" is employed for practical metal plating and contains organic additives whose concentrations are controlled within ranges, whereas the corresponding "supporting electrolyte" typically has substantially the same inorganic composition as the plating bath. In some cases, a supporting electrolyte may contain one or more organic additives at predetermined concentrations, or may have an inorganic composition that differs from that of the plating bath. The term "plating solution" is generic, encompassing any solution used for metal electrodeposition. The term "bleed and feed" refers to the practice of continuously or periodically removing and replacing a portion of a plating bath with fresh plating solution to avoid accumulation of detrimental species in the plating bath.

In this document, the term "standard addition" generally means addition of a predetermined quantity of a breakdown product or an additive to a predetermined volume of a supporting electrolyte or a measurement solution. The predetermined quantity may be a predetermined weight of the breakdown product or a predetermined volume of a standard solution of the breakdown product. Such standard addition does not change the name of the supporting electrolyte so that a plating rate parameter may be measured before and after a standard addition of the breakdown product to the supporting electrolyte. The symbol "M" means molar concentration. The "volume fraction" is the volume of a standard breakdown product solution added to the supporting electrolyte divided by the total volume of the supporting electrolyte after the addition. Calibration data are typically handled as calibration curves or plots but such data may be tabulated and used directly, especially by a computer, and the terms "curve" or "plot" include tabulated data.

Voltammetric data may be generated by scanning the electrode potential at a constant rate or by stepping the potential, or by a combination of potential scanning and stepping. A "cyclic voltammogram" is a plot of current or current density (on the y-axis) versus the working electrode potential (on the x-axis) typically obtained by cycling the working electrode potential with time between fixed negative and positive limits. A "potentiostat" is an electronic device for controlling the potential of a working electrode by passing current between the working electrode and a counter electrode so as to drive the working electrode to a desired potential relative to a reference electrode. Use of a potentiostat avoids passing appreciable current through the reference electrode, which might change its potential. Operation in the three-electrode mode may also reduce errors in the electrode potential associated with the resistive voltage drop in the electrolyte.

The present invention provides a method for determining the concentration of an additive breakdown product in a metal electroplating bath. The method is useful for analysis of additive breakdown products that affect the metal electrodeposition rate and decompose as a function of time. The method is especially useful for analysis of anti-suppressor additive breakdown products that increase the metal electrodeposition rate, but could also be applied to analysis of additive breakdown products that decrease the metal electrodeposition rate.

In the method of the present invention, a rate parameter for electrodeposition of the metal is measured at a plurality of times in the plating bath being analyzed, or in a measurement solution comprising the plating bath and a supporting electrolyte. The additive breakdown product concentration in the plating bath is determined from the slope of a plot of the metal electrodeposition rate parameter versus a time parameter. A preferred electrodeposition rate parameter is the metal stripping peak area ($A_r$) measured by CVS but other CVS rate parameters, or rate parameters measured by other methods, may be used. Preferred time parameters include CVS cycle number, logarithm of the CVS cycle number, a predetermined time within each CVS cycle and logarithm of the predetermined time, but other time parameters, such as a quadratic function of time, may also be used. The preferred time parameter may vary depending on the type of plating bath, the organic additives present, and age of the plating bath. For one commercial acid copper plating bath, the preferred time parameter was found to be the CVS rate parameter when the bath was fresh, and the logarithm of the CVS rate parameter for the aged bath.

The concentration of the breakdown product changes as a function of time during the measurement and must, therefore, be referenced to a predetermined time, the time at the beginning of the analysis, for example. The breakdown product concentration at an earlier time, when the bath sample was withdrawn from the plating bath, for example, may be determined by extrapolating the electrodeposition rate parameter vs. time parameter plot. Preferably, the breakdown product analysis is performed on an isolated sample of the plating bath to avoid errors associated with changes in the breakdown product concentration produced, for example, by reactions at the relatively large electrodes typically used in production plating baths. Measurements according to the present invention may, however, be performed directly in the plating bath.

The slope of an electrodeposition rate parameter vs. time parameter plot may be utilized as a relative measure of the concentration of an additive breakdown product in a plating bath at a predetermined time. For example, a plating bath may be operated so as to maintain this slope, measured for bath samples at a predetermined time after withdrawal from the bath, within a range of values predetermined to provide acceptable deposit properties.

Alternatively, the absolute concentration of an additive breakdown product in a plating bath at a predetermined time may be determined by reference to a standard curve. The standard curve may be generated by measuring the electrodeposition rate parameter for a supporting electrolyte of the plating bath at a plurality of times for a plurality of standard additions of the breakdown product to the supporting electrolyte. Typically, the electrodeposition rate parameter is measured in the supporting electrolyte as a function of time after standard addition of the breakdown product to provide a standard curve of the slope of electrodeposition rate parameter vs. time parameter plot as a function of the concentration of the breakdown product added to the supporting electrolyte. The absolute concentration of the breakdown product in the plating bath sample at the beginning of the analysis (or another predetermined time) is determined by comparing the slope of the electrodeposition rate parameter vs. time parameter plot for the plating bath sample to the standard curve.

The analysis of the present invention may be performed directly on a sample of a plating bath (or on the plating bath itself). In this case, concentrations of bath components other than the additive breakdown product being analyzed are preferably maintained within their normal control ranges so as to minimize interference with the breakdown product analysis. Standard addition of some bath components to the plating bath sample may be employed to ensure that their concentrations are maintained within a range for which interference with the analysis is minimized. For example, standard addition of suppressor additive to acid copper bath samples may be employed to ensure that the suppressor concentration is within the full suppression range for which variations in the suppressor concentration have minimal effect on the copper electrodeposition rate. The suppressor species added to the plating bath sample may be a different species than that used in the plating bath. Suitable suppressor species include polyethylene glycol, polypropylene glycol, and polyethylene glycol monomethylether, for example.

The analysis of the present invention may also be performed on a measurement solution comprising the plating bath being analyzed and a supporting electrolyte at a predetermined volume ratio. In addition, calibration to provide an absolute breakdown product concentration generally involves standard addition of the breakdown product to a supporting electrolyte. In either case, the supporting electrolyte preferably has the same inorganic composition as the plating bath. The supporting electrolyte may, however, contain different inorganic constituents or different inorganic constituent concentrations than those in the plating bath if such compositional differences do not produce substantial changes in the metal electrodeposition rate or the rate at which the additive breakdown product decomposes. The supporting electrolyte may also contain one or more organic additives at predetermined concentrations. A preferred supporting electrolyte for analysis of an acid copper plating bath includes sufficient suppressor additive to ensure full suppression of the copper electrodeposition rate. Anti-suppressor and leveler additives may also be added to an acid copper supporting electrolyte to minimize interference with the anti-suppressor breakdown product analysis.

The metal deposition rate for the method of the present invention is preferably determined by cyclic voltammetric stripping (CVS) or cyclic pulse voltammetric stripping (CPVS). As used in this document, the term "cyclic voltammetric stripping" or "CVS" implicitly includes the CPVS method, which is a variation of the CVS method. Likewise, the term "CVS rate parameter" includes the analogous CPVS voltammetric rate parameters.

In the CVS method, the potential of an inert working electrode, typically platinum, is cycled in a plating solution at a constant rate between fixed potential limits so that a metal is alternately electrodeposited on the electrode surface and anodically stripped back into the solution. Preferably, a rotating disk electrode configuration is used for the working electrode to control solution mass transport so as to improve the sensitivity and reproducibility of the analysis results. The metal deposition rate is preferably measured via the metal stripping peak area at a constant electrode rotation rate ($A_r$) but may also be determined from the stripping peak height, or from the electrode impedance, current (including average current), or integrated current (i.e., charge) measured for a predetermined cathodic potential or potential range (with or without electrode rotation). All of these rate parameters provide a relative measure of the metal electrodeposition rate that can readily be used for comparisons only when the measurement conditions are the same. Improved reproducibility and accuracy may be provided by using the normalized CVS rate parameter, $A_r/A_r(0)$, which is the ratio of the stripping peak area for a plating solution after a standard addition to that for plating solution without additions.

For CVS analyses, a plurality of potential cycles is typically employed to condition the working electrode surface so as to provide reproducible results. In this case, data are accepted only when a steady-state condition is reached, as indicated by substantially equivalent voltammograms or voltammetric features on successive cycles. Typically, steady state is indicated by successive $A_r$ values that differ by less than a predetermined percentage (0.5%, for example).

The inert working electrode for CVS measurements may be comprised of any suitable electrically conducting material that is stable in the plating solution under the conditions used for the voltammetric analysis but is preferably comprised of a noble metal, for example, platinum, iridium, gold, osmium, palladium, rhenium, rhodium, ruthenium, and alloys thereof. Other oxidation-resistant metals and alloys, stainless steel, for example, might also be used as working electrode materials. A typical CVS rotating disk electrode is comprised of a platinum metal disk (3-5 mm diameter), with an electrical contact wire on the backside, embedded flush with one end of an insulating plastic cylinder (10-20 mm diameter). The rotating disk electrode may be fabricated by press fitting the metal disk into a hole in the plastic but is preferably fabricated by hot pressing, which forms a seal between the metal and the plastic that prevents intrusion of the solution. A suitable plastic for mounting rotating disk electrodes by hot pressing is polytrifluorochloroethylene (Kel-F®). The rotating disk electrode is usually rotated at a constant rate (100-10,000 rpm) but the electrode rotation may be modulated with time.

Precise control over the working electrode potential needed for CVS measurements is typically provided via an electronic potentiostat in conjunction with a counter electrode and a reference electrode, e.g., silver-silver chloride (SSCE), mercury-mercury sulfate, or saturated calomel electrode (SCE). A double junction may be used to extend the life of the reference electrode by inhibiting intrusion of plating bath species. The counter electrode may be a reactive metal or an inert metal. Practically any electrical conductor that resists oxidation and reduction in the plating solution may be used as an inert counter electrode, including metals, alloys and conducting oxides. A preferred inert counter electrode material is 316 stainless steel, which is highly oxidation-resistant and relatively inexpensive, but other types of stainless steel or other oxidation-resistant alloys (Inconel, for example) may also be used. Other suitable inert counter electrode materials include noble metals, for example, platinum, iridium, gold, osmium, palladium, rhenium, rhodium, ruthenium, and alloys thereof.

Metal deposition rates according to the present invention may also be measured by methods other than CVS, including those based on measurements of the ac impedance of the cathode, for example. The same electrode materials and configurations can be used for such alternative methods. Although the precision and reproducibility of the analysis might be degraded, current measurements reflecting the metal deposition rate could also be made at a stationary electrode and/or without potential cycling. If a stationary working electrode is used for the anti-suppressor breakdown product analysis of the present invention, the hydrodynamic conditions at the electrode surface are preferably controlled, by stirring or pumping the solution, for example.

The method of the present invention may be used, for example, to measure the concentration of the 3-mercaptopropylsulfonic acid (MPSA) breakdown product of the bis(sodiumsulfopropyl)disulfide (SPS) anti-suppressor additive in an acid copper sulfate plating bath. In the presence of oxygen, MPSA decomposes rapidly in acid copper baths so that the CVS stripping peak area ($A_r$) decreases on successive CVS cycles. A plot of $A_r$ vs. CVS cycle number (or time) or logarithm of CVS cycle number (or time) is typically linear and the slope of the plot may be calibrated to provide a measure of the MPSA concentration at a specific CVS cycle number or time, at the beginning of the analysis, for example. The MPSA concentration at an earlier time, when the bath sample was withdrawn from the plating bath, for example, may be determined by extrapolation of the $A_r$ vs. (CVS cycle number) or logarithm (CVS cycle number) plot.

The composition of acid copper electroplating baths varies greatly depending on the type of bath and the supplier. High-acid baths typically contain 40-100 g/L copper sulfate, 140-240 g/L sulfuric acid and 25-100 ppm chloride ion. Low-acid baths typically contain 125-200 g/L copper sulfate, 1-40 g/L sulfuric acid and 25-100 ppm chloride ion. Acid copper plating bath additives are generally proprietary formulations supplied in the form of solutions that may contain more than one additive species or combination of additives. The chemical nature and concentrations of the additive species are typically not specified and may be changed from time to time by the supplier without notice.

Since chloride exerts a strong effect on the functioning of suppressor additives used in acid copper baths, its concentration should, if necessary, be adjusted to be within the appropriate range (typically, 25 to 100 ppm) in the plating bath sample being analyzed, and in the supporting electrolyte used for calibration. Variations in the chloride, sulfuric acid and copper ion concentrations within the ranges recommended by the bath supplier usually have a negligible effect on CVS analysis results.

Copper electrodeposition rate measurements are preferably made at a constant temperature (within ±0.5° C.) since errors resulting from temperature variations may be significant. Acid copper baths are typically operated at ambient temperature but measurements may be made at a higher or a lower temperature. The accuracy of CVS rate parameter measurements may be improved by employing a slightly elevated solution temperature (3° or 4° C. above room temperature, for example) that can be more consistently maintained. The effect of temperature on the additive decomposition rate should be taken into account. Metal deposition rate measurements for analysis and calibration solutions should be performed at the same temperature.

Best results for the analysis of the present invention are provided by optimizing the CVS measurement parameters for the particular bath type and additive system employed. The key CVS measurement parameters and their typical ranges for acid copper baths include the electrode rotation rate (100-10,000 rpm), potential scan rate (10-1000 mV/s), negative potential limit (−0.05 to −0.5 V vs. SSCE) and positive potential limit (1.4 to 1.8 V vs. SSCE). A positive potential limit of relatively high voltage (in the oxygen evolution region) is typically used so that organic species adsorbed on the electrode surface are removed by electrochemical oxidation on each cycle, which provides more reproducible results. Additional CPVS measurement parameters include the potentials and hold times for the pulses or steps used.

Optimization of the CVS measurement parameters typically involve variations in the negative potential limit and/or the potential scan rate, which determine the amount of metal deposited on the electrode and thus the sensitivity of the rate parameter. Another key optimization parameter is the electrode rotation rate, which determines the rate at which additive species and breakdown products are replenished at the electrode surface as they are consumed during metal electrodeposition. Typically, the rotation rate is increased for detection of a species present at relatively low concentration.

DESCRIPTION OF A PREFERRED EMBODIMENT

In a preferred embodiment, the concentration of the 3-mercaptopropylsulfonic acid (MPSA) breakdown product of the bis(sodiumsulfopropyl)disulfide (SPS) anti-suppressor additive in an acid copper sulfate plating bath is determined from the decrease in the CVS stripping peak area ($A_r$) resulting from MPSA decomposition in the plating bath. Preferably, the MPSA concentration in the plating bath at the beginning of the analysis is determined by comparing the slope of a plot of $A_r$ vs. (CVS cycle number) or Log (CVS cycle number) for a plating bath sample to a corresponding calibration curve generated by standard addition of MPSA to a bath supporting electrolyte. The MPSA concentration at the time the bath sample was withdrawn from the plating bath is then determined by extrapolation of the analysis results. The bath supporting electrolyte preferably has substantially the same inorganic composition as the plating bath and contains predetermined concentrations of suppressor and anti-suppressor additives. Preferred suppressor additives for addition to the supporting electrolyte include polyethylene glycol, polypropylene glycol, and polyethylene glycol monomethylether.

A preferred procedure for CVS voltammetric measurements is to cycle the potential of a rotating platinum disk electrode relative to a reference electrode between fixed positive and negative potential limits via a potentiostat and a counter electrode. Measurements are preferably made at a constant temperature (within ±5° C.). The concentrations of inorganic components and organic additives in the plating bath are preferably maintained within the ranges recommended by the bath supplier.

Prior to the additive breakdown product analysis, the potential of the working electrode is preferably cycled (over the potential range used for the analysis) in the bath supporting electrolyte to condition the electrode surface. For both the electrode conditioning and the analysis, the potential of the working electrode is preferably cycled until successive $A_r$ values differ by less than a predetermined percentage (typically 0.5%).

The efficacy of the present invention was demonstrated via CVS measurements on an acid copper sulfate supporting electrolyte after addition of MPSA at various concentrations. The supporting electrolyte contained 40 g/L Cu (added as $CuSO_4 \cdot 5H_2O$), 10 g/L $H_2SO_4$, 50 ppm chloride ion, 4.0 g/L polyethylene glycol monomethylether suppressor additive (formula weight 5000) and, in some cases, the SPS additive. The SPS and MPSA materials were purchased from Raschig Chemical (Germany). Electrolytes were prepared using deionized water.

CVS measurements were made under potentiostatic control using a Qualilab QL-10® plating bath analyzer (ECI Technology, Inc.). The solution under analysis (50 mL) was contained in a polyethylene beaker cell (open to the atmosphere). The CVS rate parameter was the copper stripping peak area ($A_r$) measured using a 4-mm diameter platinum rotating disk electrode (2500 rpm) cycled between −0.225 V and +1.575 V vs. SSCE/M (silver-silver chloride electrode modified by replacing the solution in a standard SSCE electrode with a saturated AgCl solution also containing 0.1 M KCl and 10 volume % sulfuric acid). The counter electrode was a stainless steel rod (6 mm diameter). For $A_r$ measurements, the anodic current was integrated over the potential range from the zero-current potential (at the cathodic-anodic crossover) to 0.55 V vs. SSCE/M. During CVS measurements, the solution temperature was controlled at 25° C. within ±0.5° C. Specimens of MPSA and SPS were injected into the cell at the positive limit in the CVS cycle. The effects of the commercial Viaform™ (Enthone Inc.) and Ultrafill™ (Shipley, Inc.) additives (at normal concentrations) were also investigated.

Figure 2:
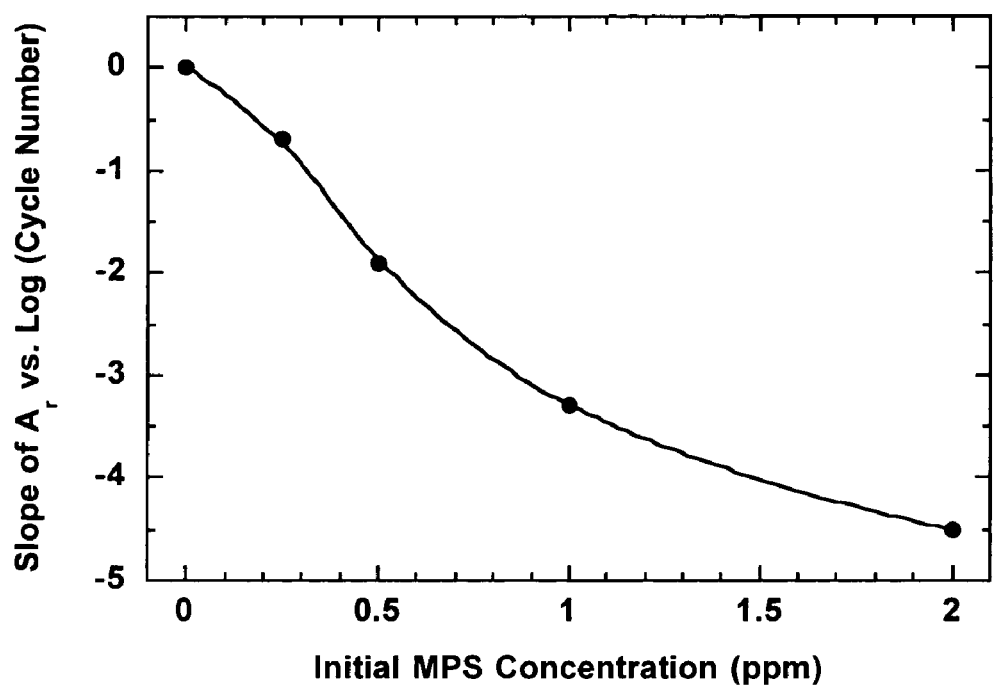
FIG. 2 shows the dependence of the slope of the $A_r$ vs. Log (CVS cycle number) plots of FIG. 1 on the concentration of MPSA added to the acid copper supporting electrolyte containing 1.0 ppm of the SPS additive.

FIG. 1 shows plots of the CVS rate parameter $A_r$ vs. Log (CVS cycle number) as a function of initial MPSA concentration for acid copper supporting electrolyte containing 1.0 ppm of the SPS additive. The linearity of these plots indicates that the decrease in $A_r$ with time is exponential. The theoretical basis for this empirical relationship would be difficult to ascertain from the present data since the measured copper deposition rate is a composite for a range of potentials, and both electrochemical and chemical processes may be involved in the decomposition process. Nonetheless, as shown in FIG. 2, the slope of such plots provides a measure of the initial MPSA concentration. Especially for higher MPSA concentrations for which the MPSA decomposition rate is high, analysis of production samples should be corrected for the time lag between sampling and analysis. This correction can be made by extrapolation of $A_r$ vs. Log (CVS cycle number) plots. For such an extrapolation to be valid, the composition of the supporting electrolyte used for the analysis should closely approximate the composition of the plating bath being analyzed.

Figure 3:
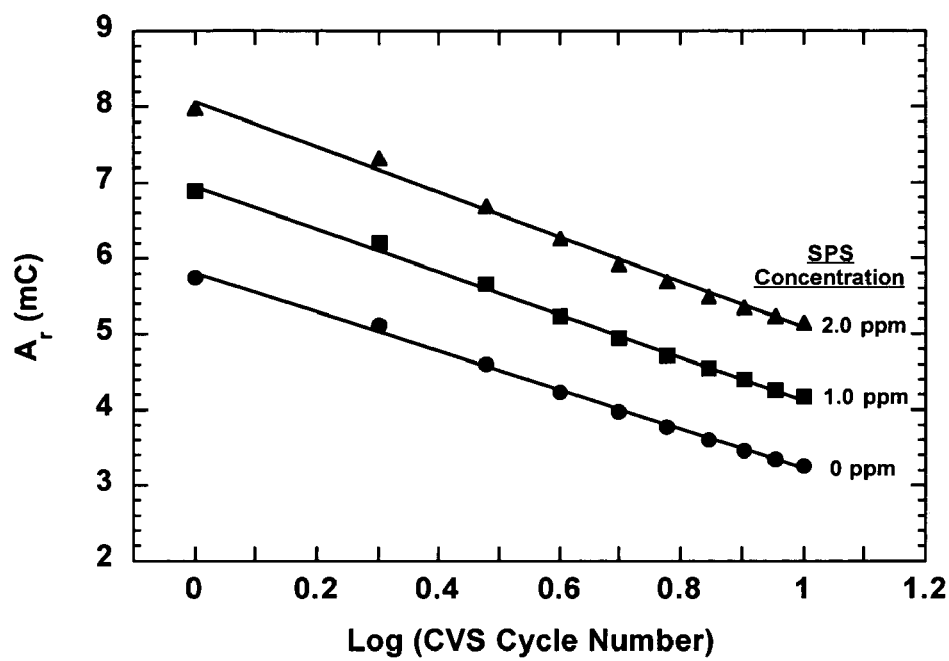
FIG. 3 shows the effect of SPS concentration on $A_r$ vs. Log (CVS cycle number) curve for acid copper supporting electrolyte with 1.0 ppm MPSA added.

FIG. 3 illustrates that the SPS concentration affects the CVS stripping peak area ($A_r$) but has no significant effect on the slope of plots of $A_r$ vs. Log (CVS cycle number). Thus, the MPSA analysis utilizing this slope is not affected by the SPS concentration.

Figure 4:
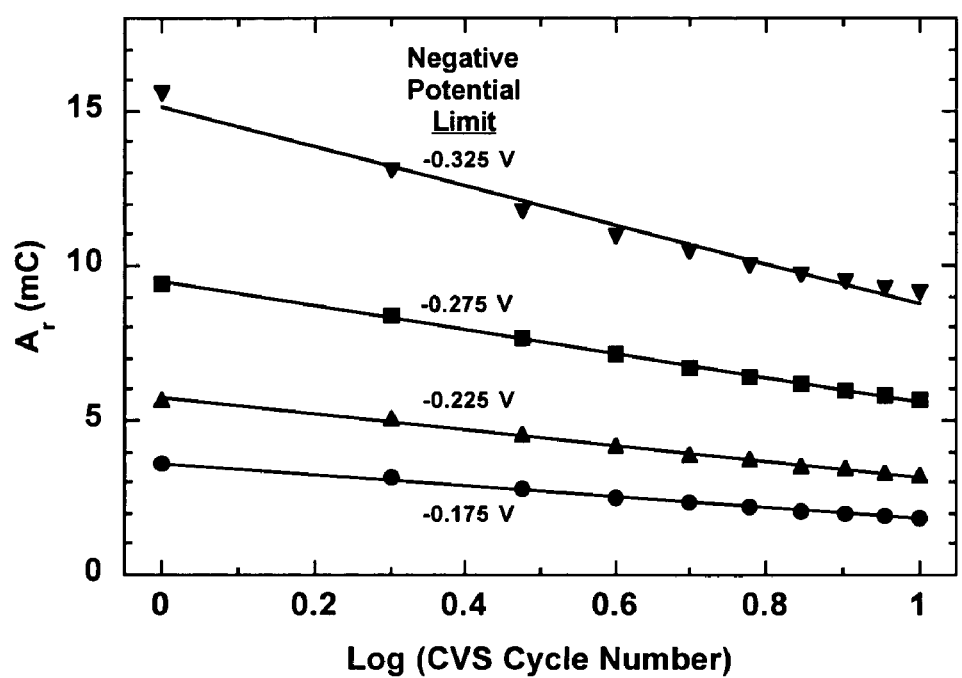
FIG. 4 shows plots of $A_r$ vs. Log (CVS cycle number) as a function of the CVS negative potential limit for acid copper supporting electrolyte containing 1.0 ppm MPSA.
Figure 5:
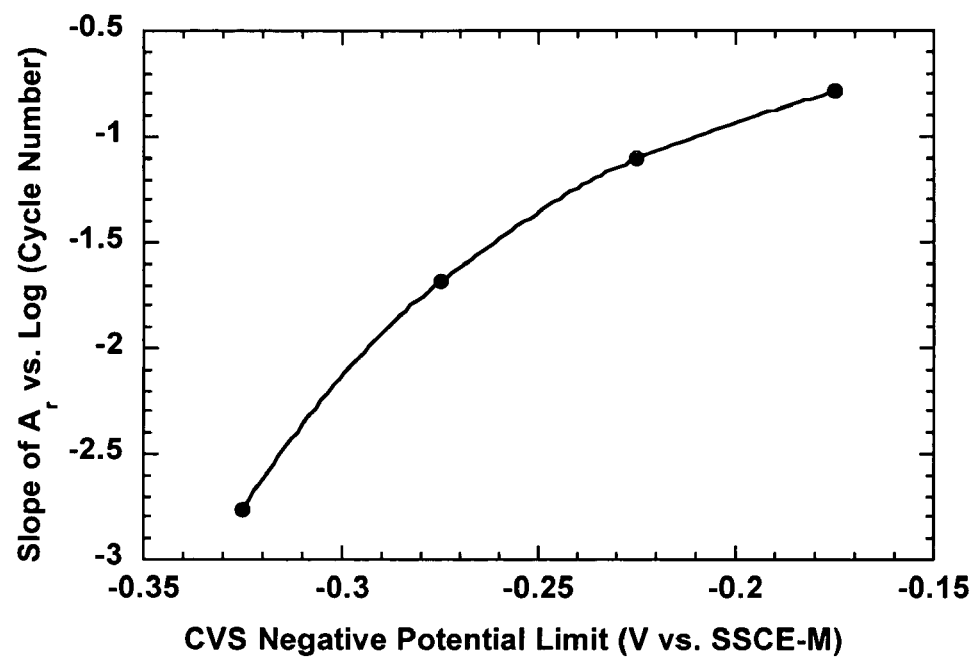
FIG. 5 shows a plot of the slopes of plots of $A_r$ vs. Log (CVS cycle number) from FIG. 4 as a function of the CVS negative potential limit for acid copper supporting electrolyte containing 1.0 ppm MPSA.

FIG. 4 illustrates the effect of negative potential scan limit on plots of $A_r$ vs. Log (CVS cycle number). Linear plots are obtained in all cases, although the slopes vary. FIG. 5 shows the dependence of the slope on the negative potential limit. These results show that the negative potential limit must be held constant for the MPSA analysis.

The preferred embodiments of the present invention have been illustrated and described above. Modifications and additional embodiments, however, will undoubtedly be apparent to those skilled in the art. Furthermore, equivalent elements may be substituted for those illustrated and described herein, parts or connections might be reversed or otherwise interchanged, and certain features of the invention may be utilized independently of other features. Consequently, the exemplary embodiments should be considered illustrative, rather than inclusive, while the appended claims are more indicative of the full scope of the invention.

We claim:

1. A method for measuring the concentration of an additive breakdown product in a plating bath for electrodepositing a metal, comprising the steps of:
    measuring a rate parameter for electrodeposition of the metal at a plurality of times in the plating bath;
    determining the slope of a plot of the rate parameter versus a time parameter; and
    utilizing the slope of the plot as a relative measure of the concentration of the additive breakdown product in the plating bath at a predetermined time.

2. The method of claim 1, wherein the breakdown product is 3-mercaptopropylsulfonic acid.

3. The method of claim 1, wherein the metal is copper and the plating bath is an acid copper plating bath comprising anions selected from the group consisting of sulfate, chloride, bromide, iodide, fluoroborate, sulfamate, alkylsulfonate, and mixtures thereof.

4. The method of claim 1, wherein the rate parameter is measured by a CVS method and is selected from the group consisting of metal stripping peak area, metal stripping peak height, current at a predetermined cathodic potential, integrated current over a predetermined cathodic potential range, and average current over a predetermined cathodic potential range.

5. The method of claim 1, wherein the time parameter is selected from the group consisting of CVS cycle number, logarithm of CVS cycle number, time, logarithm of time, and quadratic function of time.

6. The method of claim 1, wherein the rate parameter is measured by an alternating current (ac) method.

7. A method for measuring the concentration of an additive breakdown product in a plating bath for electrodepositing a metal, comprising the steps of:
    measuring a rate parameter for electrodeposition of the metal at a plurality of times in a measurement solution comprising the plating bath;
    determining the slope of a plot of the rate parameter versus a time parameter;
    providing a standard curve by measuring the rate parameter for a supporting electrolyte of the plating bath at a plurality of times for a plurality of standard additions of the breakdown product to the supporting electrolyte; and
    comparing the slope of the plot to the standard curve to determine the concentration of the additive breakdown product in the plating bath at a predetermined time.

8. The method of claim 7, wherein the measurement solution further comprises the supporting electrolyte.

9. The method of claim 7, wherein the breakdown product is 3-mercaptopropylsulfonic acid.

10. The method of claim 7, wherein the metal is copper and the plating bath is an acid copper plating bath comprising anions selected from the group consisting of sulfate, chloride, bromide, iodide, fluoroborate, sulfamate, alkylsulfonate, and mixtures thereof.

11. The method of claim 7, wherein the rate parameter is measured by a CVS method and is selected from the group consisting of metal stripping peak area, metal stripping peak height, current at a predetermined cathodic potential, integrated current over a predetermined cathodic potential range, and average current over a predetermined cathodic potential range.

12. The method of claim 7, wherein the time parameter is selected from the group consisting of CVS cycle number, logarithm of CVS cycle number, time, logarithm of time, and quadratic function of time.

13. The method of claim 7, wherein the rate parameter is measured by an alternating current (ac) method.

14. A method for measuring the concentration of an additive breakdown product in an acid copper plating bath, comprising the steps of:
    measuring a rate parameter for copper electrodeposition at a plurality of times in a measurement solution comprising the acid copper plating bath;
    determining the slope of a plot of the rate parameter versus a time parameter;
    providing a standard curve by measuring the rate parameter for a supporting electrolyte of the acid copper plating bath at a plurality of times for a plurality of standard additions of the breakdown product to the supporting electrolyte; and
    comparing the slope of the plot to the standard curve to determine the concentration of the additive breakdown product in the acid copper plating bath at a predetermined time.

15. The method of claim 14, wherein the measurement solution further comprises the supporting electrolyte.

16. The method of claim 14, wherein the breakdown product is 3-mercaptopropylsulfonic acid.

17. The method of claim 14, wherein the acid copper plating bath comprises anions selected from the group consisting of sulfate, chloride, bromide, iodide, fluoroborate, sulfamate, alkylsulfonate, and mixtures thereof.

18. The method of claim 14, wherein the rate parameter is measured by a CVS method and is selected from the group consisting of copper stripping peak area, copper stripping peak height, current at a predetermined cathodic potential, integrated current over a predetermined cathodic potential range, and average current over a predetermined cathodic potential range.

19. The method of claim 14, wherein the time parameter is selected from the group consisting of CVS cycle number, logarithm of CVS cycle number, time, logarithm of time, and quadratic function of time.

20. The method of claim 14, wherein the rate parameter is measured by an alternating current (ac) method.

21. A method for measuring the concentration of 3-mercaptopropylsulfonic acid (MPSA) in an acid copper plating bath, comprising the steps of:
   measuring a CVS rate parameter for copper electrodeposition at a plurality of times in a measurement solution comprising the acid copper plating bath;
   determining the slope of a plot of the CVS rate parameter versus a time parameter;
   providing a standard curve by measuring the CVS rate parameter for a supporting electrolyte of the acid copper plating bath at a plurality of times for a plurality of standard additions of MPSA to the supporting electrolyte; and
   comparing the slope of the plot to the standard curve to determine the concentration of MPSA in the acid copper plating bath at a predetermined time.

22. The method of claim 21, wherein the measurement solution further comprises the supporting electrolyte.

23. The method of claim 21, wherein the acid copper plating bath comprises anions selected from the group consisting of sulfate, chloride, bromide, iodide, fluoroborate, sulfamate, alkylsulfonate, and mixtures thereof.

24. The method of claim 21, wherein the CVS rate parameter is selected from the group consisting of copper stripping peak area, copper stripping peak height, current at a predetermined cathodic potential, integrated current over a predetermined cathodic potential range, and average current over a predetermined cathodic potential range.

25. The method of claim 21, wherein the time parameter is selected from the group consisting of CVS cycle number, logarithm of CVS cycle number, time, logarithm of time, and quadratic function of time.

26. A method for measuring the concentration of 3-mercaptopropylsulfonic acid (MPSA) in an acid copper plating bath, comprising the steps of:
   measuring $A_r$ at a plurality of times in a measurement solution comprising the acid copper plating bath;
   determining the slope of a plot of $A_r$ versus a time parameter selected from the group consisting of CVS cycle number, logarithm of CVS cycle number, time, logarithm of time, and quadratic function of time;
   providing a standard curve by measuring $A_r$ for a supporting electrolyte of the acid copper plating bath at a plurality of times for a plurality of standard additions of MPSA to the supporting electrolyte; and
   comparing the slope of the plot to the standard curve to determine the concentration of MPSA in the acid copper plating bath at a predetermined time.

* * * * *